United States Patent
Hassan et al.

(10) Patent No.: US 8,741,893 B2
(45) Date of Patent: Jun. 3, 2014

(54) 6,7-DIHYDRO-[1,3,4]THIADIAZOLO-[3,2-A][1,3]DIAZEPIN DERIVATIVES AND PHARMACEUTICAL COMPOSITIONS CONTAINING THE SAME AS HYPNOTIC OR ANESTHETIC AGENT AND METHOD FOR THEIR PREPARATION

(75) Inventors: Ghada S. Hassan, Riyadh (SA); Hussein I. El-Subbagh, Riyadh (SA); Mohamed A. Al-Omar, Riyadh (SA); Kamal E. H. El-Taher, Riyadh (SA); Khalid A. Al-Rashood, Riyadh (SA); Abdulrahman M. Al-Obaid, Riyadh (SA); Adel S. El-Azab, Riyadh (SA); Alaa A.-M. Abdelaziz, Riyadh (SA); Fatmah A. Al-Omary, Riyadh (SA); Mohamed M. Hefnawy, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 14/042,057

(22) PCT Filed: Apr. 4, 2012

(86) PCT No.: PCT/EP2012/001486
§ 371 (c)(1),
(2), (4) Date: Dec. 6, 2013

(87) PCT Pub. No.: WO2012/136356
PCT Pub. Date: Oct. 11, 2012

(65) Prior Publication Data
US 2014/0088090 A1    Mar. 27, 2014

(30) Foreign Application Priority Data
Apr. 8, 2011  (EP) ..................... 11161596

(51) Int. Cl.
*A61K 31/55*    (2006.01)
*C07D 513/04*   (2006.01)
*A61K 31/551*   (2006.01)
*A61K 31/381*   (2006.01)

(52) U.S. Cl.
CPC ............ *C07D 513/04* (2013.01); *A61K 31/551* (2013.01); *A61K 31/381* (2013.01)
USPC ...................................................... 514/221

(58) Field of Classification Search
CPC ... C07D 513/04; A61K 31/381; A61K 31/551
USPC ...................................................... 514/221
See application file for complete search history.

(56) References Cited

FOREIGN PATENT DOCUMENTS

DE    10320732 A1    12/2004

OTHER PUBLICATIONS

Database Registry [Online] Chemical Abstracts Service, Columbus Ohio, US; Aug. 5, 2009, XP002638048 retrieved from STN Database accession No. 1172773-60-2.
Database Registry [Online] Chemical Abstracts Service, Columbus Ohio, US; Aug. 3, 2009, XP002638049 retrieved from STN Database accession No. 1171898-18-2.
Database Registry [Online] Chemical Abstracts Service, Columbus Ohio, US; Aug. 2, 2009, XP002638050 retrieved from STN Database accession No. 1171647-95-2.
Database Registry [Online] Chemical Abstracts Service, Columbus Ohio, US; Aug. 2, 2009, XP002638051 retrieved from STN Database accession No. 1171338-80-9.
Database Registry [Online] Chemical Abstracts Service, Columbus Ohio, US; Jul. 29, 2009. XP002638052 retrieved from STN Database accession No. 1170159-13-3.
Database Registry [Online] Chemical Abstracts Service, Columbus Ohio, US; Jun. 8, 2006, XP002638053 retrieved from STN Database accession No. 887201-49-2.
Database Registry [Online] Chemical Abstracts Service, Columbus Ohio, US; Jun. 6, 2004, XP002638054 retrieved from STN Database accession No. 689746-41-6.
Database Registry [Online] Chemical Abstracts Service, Columbus Ohio, US; Jun. 4, 2004, XP002638055 retrieved from STN Database accession No. 689267-72-9.
Database Registry [Online] Chemical Abstracts Service, Columbus Ohio, US; Mar. 6, 2003, XP002638056 retrieved from STN Database accession No. 497063-92-0.
Sanger: "The Pharmacology and Mechanisms of Action of New Generation, Non-Benzodiazepine Hypnotic Agents", CNS Drugs, vol. 18 No. suppl. 1, Jan. 1, 2004 (whole document).
Krogsgaard-Larsen et al.: "GABAA Agonists and Partial Agonists: THIP (Gaboxadol) as a Non-Opioid Analgesic and a Novel Type of Hypnotic", Biochemical Pharmacology, vol. 68, No. 8., Oct. 15, 2004, pp. 1573-1580, XP004580105, (whole document).
Lloyd et al.: "Specificity Within the GABAA Receptor Supramolecular Complex: A Consideration of the New Omega 1-Receptor Selective Imidazopryidine Hypnotic Zolpidem", Pharmacology Biochemistry and Behavior, vol. 29, No. 4, Apr. 1, 1988, pp. 781-783, XP025508514, (whole document).

*Primary Examiner* — San-Ming Hui
(74) *Attorney, Agent, or Firm* — Lucas & Mercanti, LLP

(57) ABSTRACT

The present invention relates to a compound represented by formula 1 or an addition salt thereof, a pharmaceutical composition containing the compound, a method for its preparation as well as the use of the compound as an hypnotic agent or anesthetic agent:

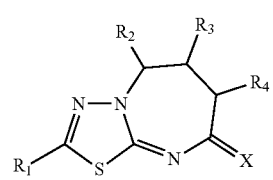

wherein each symbol is as defined in the Specification.

14 Claims, No Drawings

6,7-DIHYDRO-[1,3,4]THIADIAZOLO-[3,2-A][1,3]DIAZEPIN DERIVATIVES AND PHARMACEUTICAL COMPOSITIONS CONTAINING THE SAME AS HYPNOTIC OR ANESTHETIC AGENT AND METHOD FOR THEIR PREPARATION

The present invention relates to compounds useful as hypnotic or anesthetic agents, pharmaceutical compositions containing the compound as well as a method for their preparation.

Episodes of sleep disorders such as insomnia with its symptoms including difficulty in initiating and maintaining sleep, frequent or repetitive nocturnal arousals and early morning awakening are known since early human life. Furthermore, the ageing processes predispose deterioration of sleep that takes the form of insomnia. This disorder results in poor day time performance and reduced quality of life. Throughout his life, man attempted various means to treat insomnia by consuming alcoholic beverages and intake of some herbs or even plant parts such as opium, *cannabis, belladonna* and others.

Medical treatment of insomnia started with the introduction of barbital, and phenobarbitone. This was followed by several other drugs giving rise to what is known as the first generation of hypnotics. Thiopentale sodium and methohexitone found various uses as sedatives, hypnotics and general anaesthetics. This group enjoyed a long time of use till the introduction of chlordiazepoxide as the first drug in the second generation of hypnotics (Christensen, A. et al, *Toxicol. Appl. Pharmacol.* 1973, 26, 495-503. Those two generations of sedative-hypnotics revealed group-specific and common side effects. Barbiturates specific side effects included respiratory, renal and cardiovascular depression whereas benzodiazepines specific side effects included anterograde amnesia and menstrual disorders. The common disadvantages of the two generations included impaired day psychomotor performance, appearance of depressant residual actions, the morning-after effects e.g. headache, drowsiness, the precipitation of tolerance, dependence with the ultimate addiction and rebound insomnia after discontinuation of the drug intake (Gericke, C. et al, *J. Am. Med. Asco.* 1994, 272, 1721-1722. Rebound insomnia is characterized by prolonged sleep onset latency, an increase in intermittent wakefulness and a decrease in the total time of sleep with the consequence of a compelling force to continue drug use.

For these reasons, efforts were continued to search for an ideal hypnotic. It was thought that this goal was probably reached upon the discovery of Gaboxadol (THIP, or 4,5,6,7-tetrahydro-isoxazolo[5,4-c]pyridine-3-ol) which was introduced as a new non-benzodiazepine hypnotic (Schultz, B. et al, *Acta Pharmacol. Toxicol. (Copend.)* 1981, 49, 116-24). This was followed by the introduction of the cyclopyrrolone "Zopiclone", the imidazopyridine "Zolpidem" and the pyrazolopyrimidine "Zaleplon" (Dooley, M et al, *Drugs* 2000, 60, 413-445). This third generation was initially thought to be devoid of rebound insomnia yet later experience with the drugs revealed their inherent capabilities to exert tolerance, dependence and rebound insomnia. However, Gaboxadol does not induce tolerance, dependence or disruption of Rapid-Eye-Movement (REM) Sleep. Unfortunately, it suffered from the serious side effect of its ability to increase the duration of spontaneous Petit-mal seizures.

Furthermore, surgical procedures require the administration of several intravenous drugs to ensure hypnosis, analgesia, relaxation and control of visceral reflex responses. The use of intravenous drugs adds flexibility and permits the administration of lower doses of inhalational anesthetic agents. Intravenous anesthetic, appropriate to the requirements of surgery, became available with the introduction of thiopental. General anesthesia most often is initiated by an injection of thiopental to induce sleep prior to administration of the agents that are necessary for maintaining anesthesia during the surgical procedure. Thiopental sodium and benzodiazepines have an important place in the practice of anesthesiology. Thiopental sodium remains the standard for comparison with new agents.

Single intravenous anesthetic dose of thiopental sodium produces unconsciousness within 10-20 seconds. The depth of anesthesia may increase for up to 40 seconds then decreases progressively until consciousness returns in 20-30 minutes. However, recovery may require many hours if large dose of thiopental is administered. Thiopental is metabolized slowly in the liver, which together with other factors such as binding of thiopental by plasma proteins, changes in blood pH or changes in the distribution of blood flow may influence the depth of anesthesia, time of recovery and duration of action of thiopental. Thiopental sodium is administered intravenously. It may be injected either as a single bolus, intermittently or as a continuous infusion. The use of continuous infusion however, increases the likelihood of over dosage, with a subsequent prolonged recovery time. For single or intermittent injections of thiopental sodium, the concentration employed should not exceed 2.5% in aqueous solution. When concentration greater than 2.5% is injected extravascularly, the pain may be severe and tissue necrosis may occur. Meanwhile, following intraarterial injection of concentrated solution of thiopental, arterial endothelium and deeper layer are immediately damaged and endarterties follows, often with thrombosis exacerbated by subsequent arteriolar spasm. Vascular ischemia and even gangrene may result.

The anesthetic effect of thiopental sodium is closely parallel to its concentration in the blood reaching the brain, because the high lipid solubility of thiopental sodium allows it to cross the blood brain barrier without noticeable delay. Recovery from the anesthetic effect occurs rapidly "about 5 minutes", governed entirely by redistribution of the drug to well-perfused tissues. After the initial rapid decline, the blood concentration drops more slowly over several hours, as the drug is taken up by the body fat and metabolized. Consequently, thiopental sodium produces a long lasting hangover. A total dose of 1 g of thiopental generally should not be exceeded if prolonged recovery is to be avoided. The larger the initial dose of thiopental sodium is required, the larger the supplementary doses must be, even in patients of the same size. Patients who use large initial dose of thiopental sodium will awaken despite plasma concentration that normally would cause sleep. For this reason, thiopental sodium cannot be used to maintain surgical anesthesia, but only as an induction agent.

Recovery following the administration of thiopental should be characterized by smooth and rapid awakening to consciousness. However, if there is postoperative pain, restlessness may become evident and analgesia should be given. Thiopental and other barbiturates are poor analgesics and may even increase sensitivity to pain when administered in proper amounts. Additionally, recovery following thiopental is often accompanied by shivering as heat is generated to restore body temperature that has decreased during anesthesia and surgery. Postural hypotension may be encountered and patient should not be moved too hurriedly. Thiopental sodium produces a dose-related depression of the respiration that can be profound. Following a dose of thiopental sodium sufficient to cause sleep, tidal volume is decreased and despite a small increase of respiratory rate, the minute volume is reduced. The functional residual capacity may be reduced, especially if coughing occurs. Larger doses of thiopental sodium cause more profound changes and respiration is maintained only by movements of the diaphragm. In the presence of hemorrhage or other form of hypovolemia, circulatory instability, sepsis, toxemia or shock, the administration of a normal dose of thiopental sodium may result in hypotension, circulatory collapse and cardiac arrest. Cerebral blood flow and cerebral metabolic rate are reduced with thiopental sodium and other barbiturate. Intracerebral pressure is reduced markedly and this effect is utilized clinically in circumstances when elevated intracrineal pressures are expected. Thiopental sodium has little effect on uterine contraction, but it does cross the placenta and depress the fetus.

Hypnotic and anesthetic agents are, for example, also known from DE 103 20 732 which are based on thiazolo-[3,2-α][1,3]diazepin derivatives.

It is an object of the present invention to provide a hypnotic or anesthetic agent which overcomes the drawbacks of the prior art. Especially a compound shall be provided exhibiting potent in vivo short acting hypnotic activity, preferably in addition to in vivo potentiating effect toward known ultrashort acting hypnotics such as thiopental sodium in combination, in order to allow the use of lower doses of both to avoid undesirable side effects. Additionally, a pharmaceutical composition containing such hypnotic or anesthetic agent shall be provided, as well as a method for its preparation.

This object is achieved by the features of the independent claims. Preferred embodiments are disclosed in the subclaims.

The term "alkyl" with regard to the definition of $R_1$-$R_4$ in the compound according to formula 1 is to be understood to comprise linear and branched alkyls. The term "halo" shall comprise derivatives which are mono-, di-, tri- or poly-halosubstituted.

If possible, all substituents $R_1$-$R_4$ may be optionally further substituted, for example by halogen, amino, substituted amino, $C_1$-$C_{20}$-alkyl, $C_1$-$C_{20}$-haloalkyl, $C_1$-$C_{20}$-alkoxy or $C_1$-$C_{20}$-haloalkoxy, or mercapto, alkylthio, alkylamino, arylthio, heteroarylthio, arylamino or heteroarylamino.

In one embodiment, at least two substituents $R_1$-$R_4$, preferably $R_3$ and $R_4$ may be taken together to form an, optionally substituted, alicyclic, aryl or heteroaryl ring system.

Surprisingly, it was found that the compounds as proposed in the present invention overcome many of the disadvantages and problems that are usually accompanied with the administration of thiopental sodium as intravenous anesthetic agent, and the compounds create an intravenous anesthetic agent that not only induces anesthesia but also maintains the anesthetic state during a surgical procedure. Especially when combining compounds according to the invention with non-hypnotic doses of thiopental sodium showed very rapid onset of action and longer duration of action with no acute tolerance or noticeable side effects related to the administration of thiopental sodium alone. Thus, this preferred combination allows the use of lower doses of thiopental sodium to avoid its undesirable side effects.

1,3,4-Thiadiazolo[3,2-α][1,3]diazepine analogs could be obtained adopting published methods (Molina, P. et al, *J. Org. Chem.* 1993, 58, 5264-5270; Imming, P. et al, *Arch. Pharm.* (Weinheim) 1995, 238, 207-215). The compounds of invention and their analogs (1) are synthesized according to an inventive method, Scheme 1. The proper 2-amino-5-substituted-1,3,4-thiadiazole (2) was acylated with the suitable acid chloride derivatives (3), where Y is chlorine or bromine, preferably bromine, and anhydrous potassium carbonate in a suitable solvent, such as, for example, toluene, ethylbenzene, o-, m-, and p-xylene, octane, nonane and isopropylbenzene, preferably toluene and ethylbenzene, at temperature ranging from about 100° to 150° C., preferably 100-120° C. The products 4 can be purified by silica gel and neutral alumina chromatography. Compounds of the formula 4 were cyclized using secondary amines, such as for example, diethylamine, pyrrolidine, morpholine, piperidine, N-methylpiperazine, preferably pyrrolidine and piperidine, in a suitable solvent, such as for example toluene, ethylbenzene, o-, m-, and p-xylene, isopropylbenzene, preferably toluene, o-xylene at temperature ranging 100-180° C., preferably 120-130° C. The products 1 can be purified by silica gel and neutral alumina chromatography. The optional thiation can be done by well known methods in the art, using, for example, Lawesson's reagent, see for example Nishio T. et al., *Tetrahedron,* 1999, 55, 5017-5026; Swensson T. M. et al., *Eur. J. Med. Chem.,* 2009, 44, 4413-4425. Representative examples of such synthesis are shown in Examples 1 and 2 below.

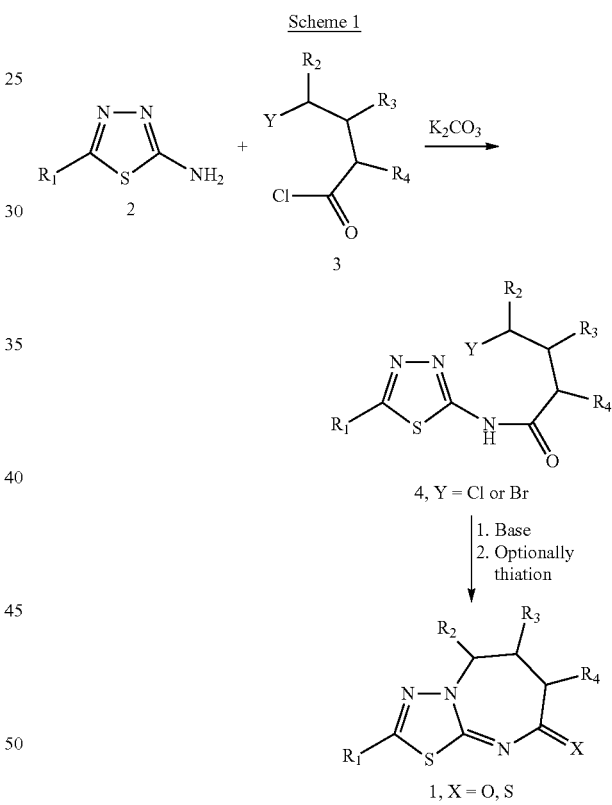

Scheme 1

Adult male Swiss albino mice (22-28 g), approximately 10-week old, were used to conduct the short acting hypnotic evaluation. They were housed in cages and kept at a temperature of 20±2° C. and a relative humidity of 55±5% with a light-dark cycle of 12 h and fed with standard diet and water ad libitum. Compounds of the formula 1 have been dissolved in dimethylsulfoxide and administered in a maximum volume of 1 ml/kg intraperitoneal whereas larger doses were suspended in 0.25% aqueous sodium carboxymethylcellulose and thoroughly homogenized and administered in volumes up to 10 ml/kg intraperitoneal. In all experiments a control group of mice was included and received intraperitoneal injections of the test compounds' vehicle.

The hypnotic activity of compounds of the formula 1 in mice was measured using the standard righting reflex method as described (Kissin, I. et al, *Anesthesiology* 1989, 70, 689-694; Enginar, N. et al, *Pharmacol. Biochem. Behav.* 1991, 40, 65-67; Matsumoto, K. et al, *Brain Res.* 1996, 708, 1-6; Nogueira, E. et al, *J. Ethopharmacology* 2000, 70, 275-280). Intraperitoneal administration of compounds of the formula 1, and thiopental sodium (Intraval sod. May & Baker LTD, England) in doses of 0.2-2 mmol/kg into mice induced hypnosis. The minimal effective doses, the onset times and the durations of sleep were recorded. The onset and durations of sleep were significantly greater than the corresponding values for thiopental sodium (P<0.05; n=6), Table 1. Representative example is shown in Example 3.

In order to study the mechanism(s) of action of the hypnotic activity of compounds of the formula 1, animals were injected intraperitoneally with the minimal hypnotic doses. Following induction of sleep, each animal was injected with caffeine as adenosine $A_1$ receptor blocker at doses up to 800 mg/kg (Fredholm, B. et al, *Eur. J. Pharmacol.* 1982, 81, 673-676); ketanserin as serotonin $S_2$ (5-$HT_2$) receptor blocker at 3 mg/kg (Janssen, P., Trends Pharmacol. Sci., 1983, 4, 198-206); picrotoxin as $GABA_A$ receptor blocker at doses up to 40 mg/kg (Macdonald, R. et al, *Epilepsy Res.* 1992, 9, 265-277); and flumazenil as non-selective but specific benzodiazepine receptor blocker at 3 mg/kg (Haefely, W., *Psychopharmacol.* 1973, 38, 73-93; Files, S. et al, Psychopharmacol. 1986, 88, 1-11; Brogden, R. et al, *Drugs* 1988, 35, 448-467); or a combination of flumazenil and picrotoxin in the above indicated doses. The animals were then carefully observed for arousal from sleep and regaining of the righting reflex. Regaining of the righting reflex following injection of any of the above treatments was considered as antagonism of the mechanism(s) involved in the induced sleep. The onset time for reversal was noted. The results of the experiments revealed the failures of caffeine, ketanserin, and flumazenil to reverse compounds of the formula 1 induced hypnosis. This proves the dis-involvement of the brain adenosinergic, serotoninergic and benzodiazepinergic systems or receptors in the induced sleep. However, the tendency of reversal of the induced sleep following the administration of picrotoxin alone or the full reversal of sleep and regaining of the righting reflex following the administration of combination of picrotoxin and flumazenil clearly proved the involvement of the combined activation of $GABA_A$ and benzodiazepine $\omega_1$ (Bnz-1) types of receptors either directly or indirectly. Representative example is shown in Example 4.

Intraperitoneal administration of compounds of the formula 1 together with a non-hypnotic dose of thiopental sodium induced sleep with a rapid onset. The durations were significantly longer than that induced by the hypnotic dose of thiopental sodium. Combined administration of one tenth of the hypnotic dose of compounds of the formula 1 (0.03-0.06 mmole/kg) and one third (0.06 mmole/kg) of thiopental sodium hypnotic dose (0.2 mmoles/kg, i.p, P<0.05, N=6) synergized each other and produced a stable sleep of rapid onset and significantly longer duration than that induced by thiopental sodium alone. The onsets and the durations of the combined treatments are shown in Table 2. Representative examples are shown in Example 5.

The $LD_{50}$ values and the therapeutic indices of compounds of formula 1 were performed. Compounds were given intraperitoneally in doses ranging from 0.1-5 mmole/kg. The animals were observed for up to 6 hours continuously and were then kept under observation for 72 hours. All behavioral changes and death during the observation periods were recorded. The percentage of death at each dose level was then calculated, and the $LD_{50}$ values were obtained (Ghosh, M., Fundamentals of Experimental Pharmacology, Scientific Book Agency, Calcutta. 1984, pp 153-158, 187-189); The Therapeutic Index of each compound was calculated following the determination of the minimal effective hypnotic dose. Representative example is shown in Example 6.

A group of 3 Swiss albino mice were used to conduct acute tolerance experiment. Each mouse received 0.4 mmol/kg of compound of formula 1 intraperitoneally, daily for 3 consecutive days. After each of the 3 administrations, the sleeping time-induced by the compound of formula 1 was recorded for each mouse. Representative example is shown in Example 7.

The biological evaluation of the new compounds of the formula 1 of the invention revealed that the compounds are short acting hypnotics. The obtained results clearly point to the discovery of a new group of hypnotics that induce their actions via interaction with $GABA_A$ and benzodiazepine $\omega_1$ receptors with additional post-hypnotic action. Thus, a new means for treatment of insomnia with all of its sleep disorders seemed to be at hand. The safety of the new compounds of the formula 1 of the invention is comparable to that of thiopental sodium and its duration is significantly longer. In addition, compounds of the invention did not show any sign of acute tolerance reported with the second (maintenance) dose of thiopental sodium. Therefore, compounds of the formula 1 of the invention have the potential use as a preanesthetic medication, induction of anesthesia, and treatment of insomnia. Combined administration of compounds of the formula 1 together with thiopental sodium, both in doses lower than the effective dose, attained the same hypnotic potency avoiding the drawbacks and side effects associated with thiopental sodium full dose administration. The durations were significantly longer than that induced by the hypnotic dose of thiopental sodium alone.

Compounds of the formula 1 of the invention, and their acid addition salts display short acting hypnotic activity. The present invention includes pharmaceutical formulations which, in addition to non-toxic, inert pharmaceutically suitable excipients, contain one or more active compounds according to the invention, or which consist of one or more active compounds according to the invention, as well as processes for the preparation of these formulations.

The present invention also includes pharmaceutical formulations in dosage units. This means that the formulations are in the form of individual parts, for example tablets, dragees, capsules, pills, and ampoules, of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semi-solid or liquid diluents, fillers and formulations auxiliaries of every kind.

Tablets, dragees, capsules, pills, granules, solutions and sprays may be mentioned as preferred pharmaceutical formulations.

Tablets, dragees, capsules and pills can contain the active compound or compounds alongside the customary excipients, such as (a) fillers and extenders, for example starches, lactose, sucrose, glucose, mannitol and silica, (b) binders, for example carboxymethylcellulose, alginates, gelatin and polyvinylpyrrolidone, (c) humectants, for example agar-agar, calcium carbonate and sodium bicarbonate, (e) solution retarders, for example paraffin, and (f) resorption accelerators, for example quaternary ammonium compounds (g) wetting agents, for example cetyl alcohol and glycerol monostearate, (h) adsorbents for example kaolin and bentonite, and (i) lubricants, for example talc, calcium stearate and magnesium stearate and solid polyethylene glycols, or mixtures of the compounds listed under (a) to (i).

The tablets, dragees, capsules and pills can be provided with the customary coatings and shells, optionally containing pacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the above mentioned excipients could also be in a micro-encapsulate form.

Solutions and emulsions for parenteral administration can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cotton seed oil, groundnut oil, maize germ oil, olive oil, caster oil and sesame oil, glycerol, glycerol-formal, tetrahydrofurfuryl alcohol, polyethylene glycol and fatty acid esters of sorbitol, or mixtures of these substances, in a sterile form which is isotonic with blood.

The therapeutically active compounds should preferably be present in the above-mentioned pharmaceutical formulations in a concentration of about 0.1 to 99.5, preferably of about 0.5 to 95% by weight of the total mixture.

The above-mentioned pharmaceutical formulations can also contain other pharmaceutical formulations; can also contain other pharmaceutical active compounds in addition to the active compounds according to the invention.

The above-mentioned pharmaceutical formulations are prepared in the customary manner according to known methods, for example by mixing the active compound or compounds with the excipient or excipients.

The present invention also includes the use of the active compounds according to the invention, and of pharmaceutical formulations which contain one or more active compounds according to the invention in human and veterinary medicine.

The actual dosage unit will be determined by such generally recognized factors as body weight of the patient and/or severity and type of pathological condition the patient might be suffering. With these considerations in mind, the dosage unit for a particular patient can be readily determined by the medical practitioner in accordance with the techniques known in the medical arts.

The precise instructions for pharmaceutical administration of the compounds and agents according to the invention necessarily depend on the requirements of the individual case, the nature of treatment, and of course the opinion of the treating physician.

It will be understood by those skilled in the art that various modifications and substitutions may be made to the invention as described above without departing from the spirit and scope of the invention. Accordingly, it is understood that the present invention has been described by way of illustration and not limitation.

EXAMPLE 1

4-Chloro-N-(5-phenyl-1,3,4-thiadiazol-2-yl)butanamide

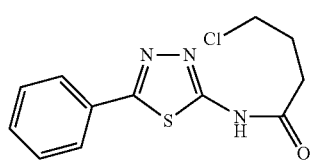 [SMILES: O=C(CCCCl)Nc1nnc(-c2ccccc2)s1]

A mixture of 5-phenyl-1,3,4-thiadiazol-2-amine (7.1 g, 0.04 mol), 4-chloro-butyryl chloride (11.3 g, 9.0 ml, 0.08 mol) and potassium carbonate (5.5 g, 0.04 mole) in toluene (100 ml) was heated under reflux for 4 hr. The toluene was then evaporated under reduced pressure. The residue was then quenched with water, stirred, and filtered. The solid obtained was washed, dried and recrystallized from toluene to give the required product (9.6 g, 85% yield), mp 159-62° C., m/e 281, 87% (consistent with molecular formula $C_{12}H_{12}ClN_3OS$, calcd. 281.04). $^1$H NMR (DMSO-$d_6$): δ 2.07-2.10 (m, 2H, —CH$_2$), 2.67-2.70 (m, 2H, —CH$_2$), 3.70-3.72 (m, 2H, —CH$_2$), 7.48-7.54 (m, 3H, ArH), 7.93-7.94 (m, 2H, ArH), 12.65 (br s, 1H, NH). $^{13}$C NMR: δ 27.9, 32.7, 45.1, 127.4, 129.8, 130.7, 131.0, 158.5, 162.4, 171.2.

EXAMPLE 2

(E) 2-Phenyl-6,7-dihydro-[1,3,4]thiadiazolo[3,2-α][1,3]diazepin-8(5H)-one (GS-62)

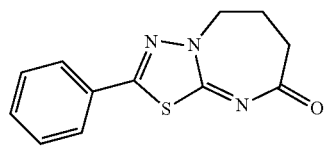 [SMILES: O=C1CCCN2N=C(c3ccccc3)SC2=N1]

A mixture of 4-chloro-N-(5-phenyl-1,3,4-thiadiazol-2-yl) butanamide (1.1 g, 0.004 mol) and piperidine (0.7 g, 0.8 ml, 0.008 mol) in toluene (50 ml) was heated under reflux for 3 h. The reaction mixture was cooled, poured into water and stirred. Toluene was separated dried and evaporated to give a crude product which was purified by repeated silica gel and neutral alumina column chromatography eluting with EtOAc/hexane (50:50 v/v) and CHCl$_3$/hexane (80:20 v/v); mp 189-92° C., m/e 245, 90% (consistent with molecular formula $C_{12}H_{11}N_3OS$, calcd. 245.06) $^1$H NMR CDCl$_3$): δ 2.33-2.36 (m, 2H, —CH$_2$), 2.75 (t, J=7.5 Hz, 2H, —CH$_2$), 4.28-4.31 (t, J=7.5 Hz, 2H, —CH$_2$), 7.46-7.52 (m, 3H, ArH), 7.94-8.10 (m, 2H, ArH). $^{13}$C NMR: δ 18.3, 31.3, 47.9, 127.4, 129.1, 130.5, 130.6, 157.4, 163.9, 173.6.

The NMR spectral data assignments of compounds of Example 1-4 are based on analysis of the $^1$H, Attached Proton Test (APT), the Distortionless Enhancement Polarization Transfer (DEPT), correlated spectroscopy (COSY), Heteronuclear Multiple Quantum Coherence Spectroscopy (HMQC), NMR spectra for each compound.

EXAMPLE 3

Measurement of the Hypnotic Effect of GS-62

Mice were initially tested for the presence of the righting reflex by placing each mouse on its back and observing the rapid correction to the normal position i.e. the righting reflex. Then groups of mice were injected intraperitoneally with various doses of the test compound and placed each separately under a 30-cm glass funnel. The animals were then observed carefully for any change in behavior such as unsteady movements, drowsiness, ataxia and loss of the righting reflex. Failure of any treated mouse to correct its posture to the normal condition of standing on its feet within one minute was considered as loss of the righting reflex and hence onset of sleep. The onset of sleep was carefully noted and recorded and the mice were continuously monitored visually and by videotaping and the duration of the sleep was noted. The end of the duration of sleep was noted by the regaining of the righting reflex 3 times within one minute albeit some drowsiness is still observed. Intraperitoneal administration of GS-62, and thiopental sodium (Intraval sod. May & Baker LTD, England) in doses of 0.2-2 mmol/kg into mice induced hypnosis. The minimal effective doses, the onset times and the durations of sleep were recorded. The onset and durations of sleep for GS-62 were significantly greater than the corresponding values for thiopental sodium (P<0.05; n=6), Table 1.

TABLE 1

Influence of the test compound GS-62 and thiopental Na on sleep in mice, $LD_{50}$ and the Therapeutic Indices values.

| Treatment | Minimal Effective Dose mmole/ kg (i.p) | Onset of sleep (minutes) | Duration of sleep minutes | $LD_{50}$ mmole/ kg (i.p) | Therapeutic Index |
|---|---|---|---|---|---|
| GS-62 | 0.4 | 6.4 ± 0.2* | 94.8 ± 5.3* | 2.65 | 6.62 |
| Thiopental Na | 0.2 | 2.0 ± 0.1 | 45 ± 3.6 | 1.22 | 6.10 |

*Significantly longer compared with that of thiopental sodium (P < 0.05, N = 6).

EXAMPLE 4

Study of the Mechanism(s) of Action of the Hypnotic Effect of GS-62

Mice were hypnotized with single dose of GS-62 (98.0 mg/kg, 0.4 mmole/kg, i.p) and allowed to sleep for 5 minutes (complete loss of the righting reflex). In such mice intraperitoneal administration of caffeine (800 mg/kg), ketanserin (3 mg/kg), flumazenil (1.2 mg/kg) did not reverse the induced sleep i.e. the righting reflex was not regained. When picrotoxin (32 mg/kg) was administered, the animals showed attempts to regain their righting reflex and showed tendency to reverse the condition of sleep by exhibiting micro-arousals. Such attempts were seen 5 minutes after administration of picrotoxin and continued for several minutes but no complete regaining of the righting reflex. However, when a combination of both picrotoxin (32 mg/kg) and flumazenil (1.2 mg/kg) was administered 5 minutes after induction of sleep by GS-62; complete reversal of sleep and regaining of the righting reflex was achieved. This was consistently observed (N=6).

EXAMPLE 5

Potentiating Effect of GS-62 to the Non Hypnotic Dose of Thiopental Sodium in Mice Combined intraperitoneal administration of GS-62 (Example 2), and thiopental sodium (Intraval sodium, May & Baker LTD, England) in doses of 0.03-0.06 mmol/kg into mice induced hypnosis. The minimal effective doses, the onset times and the durations of sleep were recorded. The onset and durations of sleep for GS-62 combined with thiopental sodium were significantly greater than the corresponding values for thiopental sodium alone (P<0.05; n=6), Table 2. GS-62 in one tenth of their minimal effective hypnotic doses (0.06 mmole/kg) can potentiate one third of the minimal effective dose (0.06 mmole/kg) of thiopental sodium.

TABLE 2

Potentiation effect of GS-62 on the non hypnotic dose of thiopental sodium in mice

| Treatment | Minimal Effective Dose (i.p) mmole/kg | Minimal Effective Dose (i.p) mg/kg | Onset of sleep (minutes) | Duration of sleep (minutes) |
|---|---|---|---|---|
| GS-62 + Thiopental Na | 0.06 | 14.7 | 7.5 ± 1.3* | 62.5 ± 5.9* |
| Thiopental Na | 0.06 | 15.9 | | |
| Thiopental Na | 0.2 | 52.8 | 2 ± 0.3 | 45 ± 3.6 |

*Significantly longer compared with that of thiopental sodium (P < 0.05, N = 6).

EXAMPLE 6

Determination of the Lethal Dose ($LD_{50}$) and the Therapeutic Index of GS-62

Male mice were divided into various groups and GS-62 (Example 2) was administered in various doses ranging from 0.1-5 mmole/kg, intraperitoneally. Following treatments, the animals were observed for up to 6 hours continuously and were then kept under observation for 72 hours. All behavioral changes and death during the observation periods were recorded. The percentage of death at each dose level was then calculated, converted to probits and the $LD_{50}$ values were calculated as outlined by (Ghosh, M., Fundamentals of Experimental Pharmacology, Scientific Book Agency, Calcutta. 1984, pp 153-158, 187-189). The Therapeutic Index of GS-62 was calculated following the determination of the minimal effective hypnotic and the $LD_{50}$ values (Table 1) by the formula:

$$\text{Therapeutic Index} = \frac{LD_{50}}{\text{Minimal effective hypnotic dose}}$$

EXAMPLE 7

Acute tolerance test was conducted following the intraperitoneal administration of GS-62 (Example 2, 98.0 mg/kg), daily for 3 consecutive days. There were no significant differences among the sleeping times after the first and the last administration of the compound. The onset and sleeping time after the first administration of the compound were 6.7±0.2 and 87±10 min., respectively; while after the last administration of the compound were 5.7±0.5 and 70±10 min., respectively.

The features disclosed in the foregoing description and in the claims may, both separately and in any combination thereof, be material for realizing the invention in diverse forms thereof.

We claim:
1. A compound according to formula 1 or an addition salt thereof:

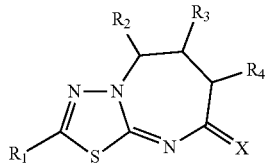

wherein $R_1$, $R_2$, $R_3$ and $R_4$ are each independently selected from hydrogen, halogen, $C_1$-$C_{20}$-alkyl, $C_1$-$C_{20}$-haloalkyl, $C_1$-$C_{20}$-alkoxy, $C_1$-$C_{20}$-haloalkoxy, aryl, heteroaryl, amino, and alkylamino, or wherein $R_3$ and $R_4$, are alicyclic, aryl or heteroaryl ring systems, which are optionally substituted by halogen, amino, $C_1$-$C_{20}$-alkyl, $C_1$-$C_{20}$-haloalkyl, $C_1$-$C_{20}$-alkoxy or $C_1$-$C_{20}$-haloalkoxy, mercapto, alkylthio, alkylamino, arylthio, heteroarylthio, arylamino or heteroarylamino, and wherein X is O or S.

2. The compound according to claim 1, wherein $R_2$ is hydrogen or $C_1$-$C_{20}$-alkyl.

3. The compound according to claim 2, wherein $R_3$ is hydrogen.

4. The compound according to claim 1, wherein $R_1$, $R_2$, $R_3$ and $R_4$ are independently aryl or heteroaryl.

5. The compound according to claim 1, wherein the compound is an addition salt of hydrochloride, hydrobromide, phosphate, nitrate, acetate, malate, succinate, fumarate, tartrate, salicylate, sorbate, lactate, p-toluene sulphate, or naphthalene-1,5-disulfonate salts.

6. A method for preparing the compound according to claim 1, comprising reacting a compound according to formula 2 with a compound according to formula 3 in the presence of $K_2CO_3$ to produce a compound according to formula 4, and then reacting the compound of formula 4 with a secondary amine to produce the compound of formula 1, as depicted in scheme 1:

Scheme 1

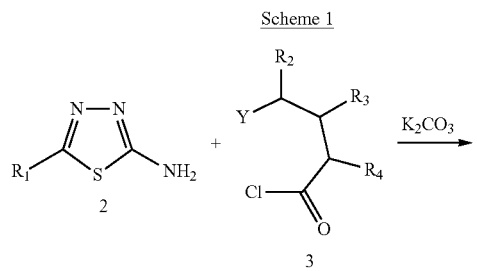

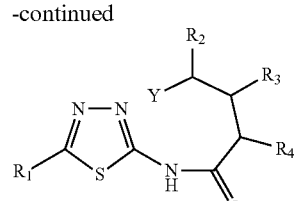

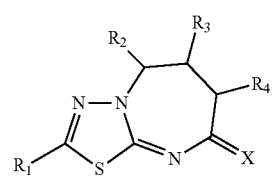

wherein Y is Cl or Br, X is O or S, and $R_1$-$R_4$ are as defined in claim 1.

7. The method according to claim 6, wherein the reaction of compound 2 and compound 3 is in the presence of a solvent.

8. The method according to claim 7, wherein the reaction of compound 4 is a cyclization reaction.

9. A pharmaceutical composition comprising the compound according to claim 1 and a pharmaceutically acceptable carrier or excipient.

10. The pharmaceutical composition according to claim 9, additionally comprising thiopental sodium.

11. A method of treating insomnia in a subject, comprising administering a sleep-inducing effective amount of the pharmaceutical composition according to claim 9 to the subject.

12. The method of claim 11, wherein the pharmaceutical composition further comprises thiopental sodium.

13. The compound according to claim 3, wherein the compound is an addition salt of hydrochloride, hydrobromide, phosphate, nitrate, acetate, malate, succinate, fumarate, tartrate, salicylate, sorbate, lactate, p-toluene sulphate, or naphthalene-1,5-disulfonate salts.

14. The method of treating insomnia in a subject according to claim 11, wherein the pharmaceutical composition administered further comprises thiopental sodium.

* * * * *